US008486038B2

(12) United States Patent
Nakahata et al.

(10) Patent No.: US 8,486,038 B2
(45) Date of Patent: Jul. 16, 2013

(54) DISPOSABLE PULL-ON GARMENT

(75) Inventors: Hiroshi Nakahata, Cincinnati, OH (US); Takaie Iba, Ashiya (JP); Thomas Luebcke, Euskirchen (DE)

(73) Assignee: The Procter & Gamble Company, Cincinnati, OH (US)

( * ) Notice: Subject to any disclaimer, the term of this patent is extended or adjusted under 35 U.S.C. 154(b) by 398 days.

(21) Appl. No.: 11/710,217

(22) Filed: Feb. 23, 2007

(65) Prior Publication Data

US 2007/0208316 A1    Sep. 6, 2007

Related U.S. Application Data

(60) Provisional application No. 60/779,173, filed on Mar. 3, 2006.

(51) Int. Cl.
*A61F 13/15* (2006.01)

(52) U.S. Cl.
USPC .............................. 604/385.24; 604/385.01

(58) Field of Classification Search
USPC ........................... 604/385.01, 385.02, 385.04
See application file for complete search history.

(56) References Cited

U.S. PATENT DOCUMENTS

| | | | | |
|---|---|---|---|---|
| 4,501,587 A * | 2/1985 | Enloe | | 604/385.23 |
| 5,580,411 A * | 12/1996 | Nease et al. | | 156/260 |
| 5,873,870 A * | 2/1999 | Seitz et al. | | 604/385.04 |
| 6,375,646 B1 * | 4/2002 | Widlund et al. | | 604/385.3 |
| 6,478,785 B1 * | 11/2002 | Ashton et al. | | 604/385.01 |
| 6,562,017 B1 * | 5/2003 | Nakaoka et al. | | 604/385.28 |
| 6,572,595 B1 * | 6/2003 | Klemp et al. | | 604/385.01 |
| 6,572,598 B1 * | 6/2003 | Ashton et al. | | 604/385.11 |
| 7,201,744 B2 * | 4/2007 | Van Gompel et al. | | 604/391 |
| 7,314,465 B2 * | 1/2008 | Van Gompel et al. | | 604/395 |
| 2002/0123730 A1 | 9/2002 | Popp et al. | | |
| 2003/0083636 A1 * | 5/2003 | Kuen et al. | | 604/385.04 |

(Continued)

FOREIGN PATENT DOCUMENTS

| | | |
|---|---|---|
| EP | 1 639 908 A1 | 3/2006 |
| JP | 2003-250826 A | 9/2003 |

OTHER PUBLICATIONS

International Search Report.

*Primary Examiner* — Susan Su
(74) *Attorney, Agent, or Firm* — Thibault Fayette; Laura L. Whitmer

(57) ABSTRACT

A disposable pull-on garment to be contained in a package is disclosed. The pull-on garment has a waist opening and leg openings, and has a longitudinal centerline and a transverse centerline. The pull-on garment comprises a main portion and side portions extending transversely outwardly from the main portion. The pull-on garment has longitudinal side contour lines to define a transverse width of the pull-on garment. The pull-on garment has a first transverse width between the longitudinal side contour lines at the waist opening and a second transverse width between the longitudinal side contour lines at the side portions. The second transverse width is greater than the first transverse width and is the greatest transverse width at the side portions in a flat contracted and unfolded condition of the pull-on garment. The side portions are folded along a folding line toward the longitudinal centerline when the pull-on garment is contained in a package such that the second transverse width decreases and the difference between the first transverse width and the second transverse width decreases when the side portions are folded compared with when the side portions are unfolded.

9 Claims, 15 Drawing Sheets

U.S. PATENT DOCUMENTS

| | | |
|---|---|---|
| 2004/0112518 A1 | 6/2004 | Rossier et al. |
| 2005/0107764 A1 | 5/2005 | Matsuda et al. |
| 2006/0218700 A1 | 10/2006 | Uda |
| 2007/0208318 A1* | 9/2007 | Loritz et al. ............. 604/385.22 |
| 2010/0280472 A1* | 11/2010 | Takeuchi et al. .............. 604/367 |

* cited by examiner

DISPOSABLE PULL-ON GARMENT

CROSS REFERENCE TO RELATED APPLICATION

This application claims the benefit of U.S. Provisional Application No. 60/779,173, filed Mar. 3, 2006.

FIELD OF THE INVENTION

The present invention relates to disposable pull-on garments which are donned by inserting the wearer's legs into the leg openings and sliding the garment up into position about the lower torso.

BACKGROUND OF THE INVENTION

Infants and other incontinent individuals wear disposable absorbent articles such as diapers to receive and contain urine and other body exudates. Absorbent garments having fixed sides (e.g., training pants or pull-on diapers) have become popular for use on children able to walk and often who are toilet training. The pull-on garment has a waist opening and a pair of leg openings and typically comprises a main portion containing an absorbent core therein and side portions extending transversely outwardly from the main portion. Because of the side ear panel transversely extending from the main portion, a typical pull-on garment has a "T" shape in which the torso portion of the garment is transversely wider than the crotch portion of the garment when the garment is in a flat uncontracted and unfolded condition.

In addition, many disposable pull-on garments use elastic elements secured in an elastically contractible condition in the waist and/or leg openings. Typically, in order to insure full elastic fit about the leg and the waist such as is provided with durable undergarments, the leg openings and waist opening are encircled with elasticized bands of rubber or other materials positioned along the curve of the opening. The elasticized materials contract the leg openings and waist opening and deform the shape of the garment. Specifically, because the garment is typically designed to provide the waist opening with a sufficient stretchability, the portion of the garment around the waist opening contracts and deforms much more than the rest of the garment. The elasticized materials provided around the waist opening also transversely contract and deform a portion of the absorbent core adjacent to the waist opening. As a result, the absorbent core which was originally, e.g., rectangle becomes deformed such that the longitudinal side edge of the absorbent core adjacent to the waist opening inclines toward the longitudinal centerline of the garment and the transverse width of the absorbent core adjacent to the waist opening is less than that of the crotch portion of the absorbent core.

An array of such garments is finally packaged into a package comprising, e.g., a flexible thin plastic film for shipment. Because of the original "T" shape of the garment in a flat uncontracted and unfolded condition and the garment shape deformed by the elasticized materials as explained above, the package containing an array of the pull-on garments does not form a well-balanced parallelepiped and stackability of packages deteriorates. While it is conceived that the ear portion of the garment is folded along the longitudinal side edge of the absorbent core, the absorbent core has been deformed due to the elasticized materials and the longitudinal side edge of the absorbent core has been also deformed to incline as explained above. Therefore, folding the ear panel along the longitudinal side edge of the absorbent core does not necessarily provide the garment with an advantageous shape to improve stackability of package.

Based on the foregoing, there is a need for a disposable pull-on garment to provide an improved stackability of package containing an array of the garment which is deformed by elasticized materials. None of the existing disposable pull-on garment provides all of the advantages and benefits of the present invention.

SUMMARY OF THE INVENTION

The present invention is directed to a disposable pull-on garment contained in a package. The pull-on garment has a waist opening and leg openings, and has a longitudinal centerline and a transverse centerline. The pull-on garment comprises a main portion and side portions extending transversely outwardly from the main portion. The pull-on garment has longitudinal side contour lines to define a transverse width of the pull-on garment. The pull-on garment has a first transverse width between the longitudinal side contour lines at the waist opening and a second transverse width between the longitudinal side contour lines at the side portions. The second transverse width is greater than the first transverse width and is the greatest transverse width at the side portions in a flat contracted and unfolded condition of the pull-on garment. The side portions are folded along a folding line toward the longitudinal centerline when the pull-on garment is contained in a package such that the second transverse width decreases and the difference between the first transverse width and the second transverse width decreases when the side portions are folded compared with when the side portions are unfolded.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). The pull-on garment is also preferably "absorbent" to absorb and contain the various exudates discharged from the body. A preferred embodiment of the pull-on garment of the present invention is the disposable absorbent pull-on garment, pull-on diaper 20, shown in FIG. 1. As used herein, the term "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.)

Figure 1:
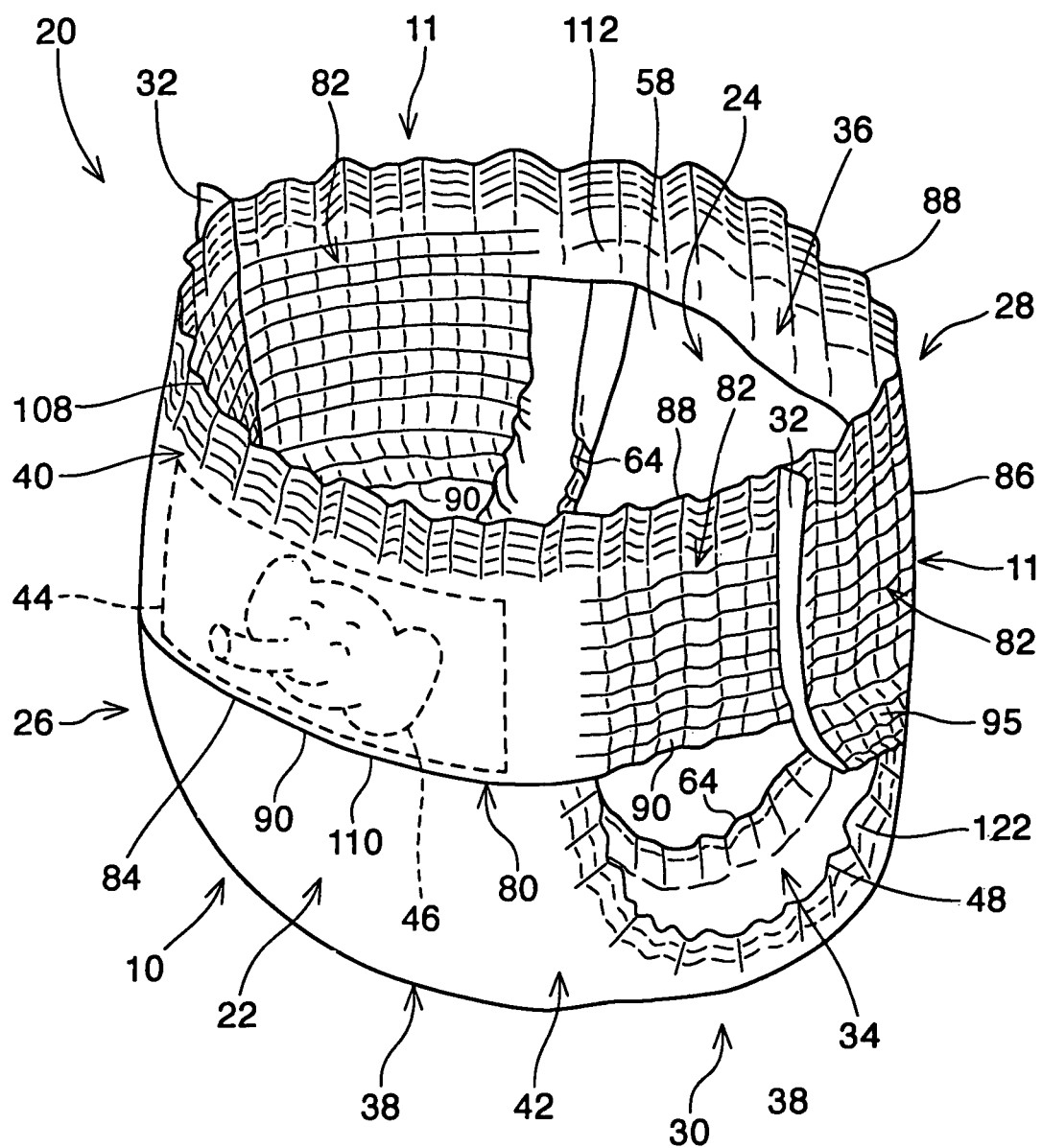
FIG. 1 is a perspective view of the disposable pull-on garment of the present invention in a typical in-use configuration.
Figure 13:
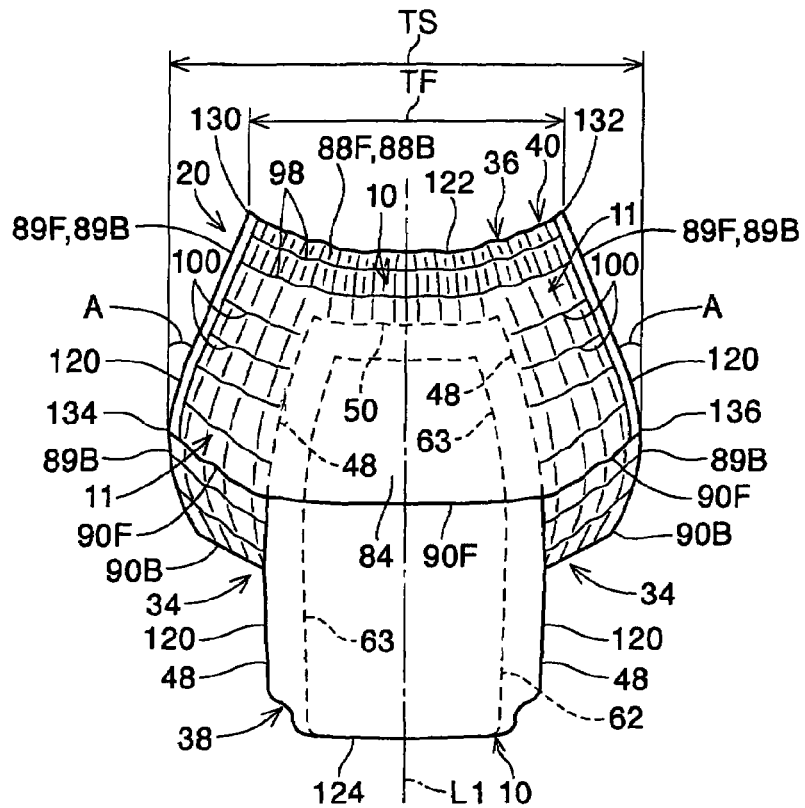
FIG. 13 is a schematic front view of the assembled pull-on garment in its contracted condition showing the first transverse width and the second transverse width.
Figure 14:
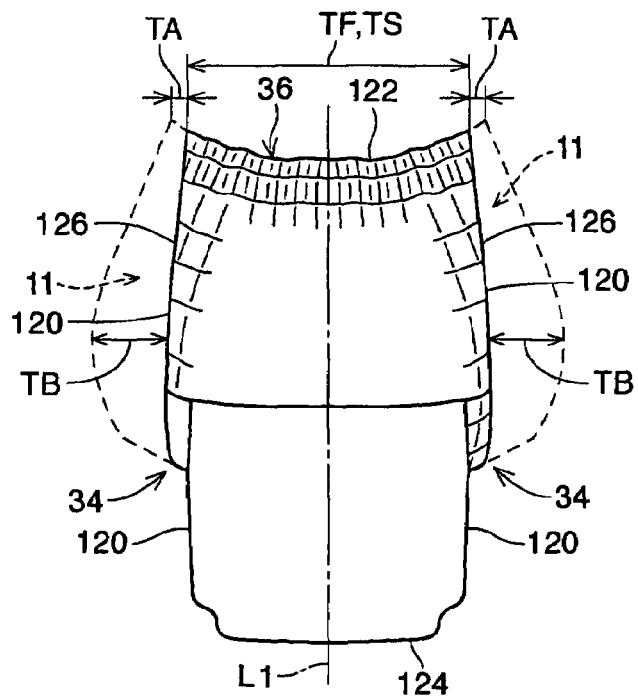
FIG. 14 is a schematic front view of the assembled pull-on garment with the side portion folded.

FIG. 1 is a perspective view of the pull-on diaper 20 of the present invention. The pull-on diaper 20 has a longitudinal centerline L1 and a transverse centerline T1 (refer to FIG. 2 as well). The pull-on diaper 20 has an outer surface 22, an inner surface 24 opposed to the outer surface 22, a front region 26, a back region 28, a crotch region 30, and seams 32 which join the front region 26 and the back region 28 to form two leg openings 34 and a waist opening 36. Also referring to FIG. 3, the diaper 20 comprises a main portion 10 and side portions 11. The main portion 10 extends longitudinally along the longitudinal centerline L1 (shown in FIG. 2) from the front region 26 through the crotch region 30 to the back region 28. The main portion 10 comprises a front main portion 12, a back main portion 13 and a crotch main portion 14 therebetween. The side portion 11 extends transversely outwardly from the main portion 10. The side portion II comprises a front side portion 15 in the front region 26 and a back side portion 16 in the back region 28. The diaper 20 has longitudinal left and right side contour lines 120 and transverse waist and crotch contour lines 122, 124 when the diaper 20 is viewed from the front or the back (refer to FIGS. 9, 13 and 14 for example). The longitudinal left and right side contour lines 120 specifically define the transverse width of the diaper 20. The term "contour line" means an outline representing or bounding the shape of the diaper 20. Therefore, the contour line varies with the form of the diaper 20. For example, while the longitudinal side contour line 120 is partly formed with the side edges 89F, 89B of the belt 40 as shown in FIG. 13 when the diaper 20 is contracted and unfolded, the longitudinal side contour line 120 is partly formed with the folding line 126 as shown in FIG. 14 when the diaper 20 is contracted and folded.

Figure 2:
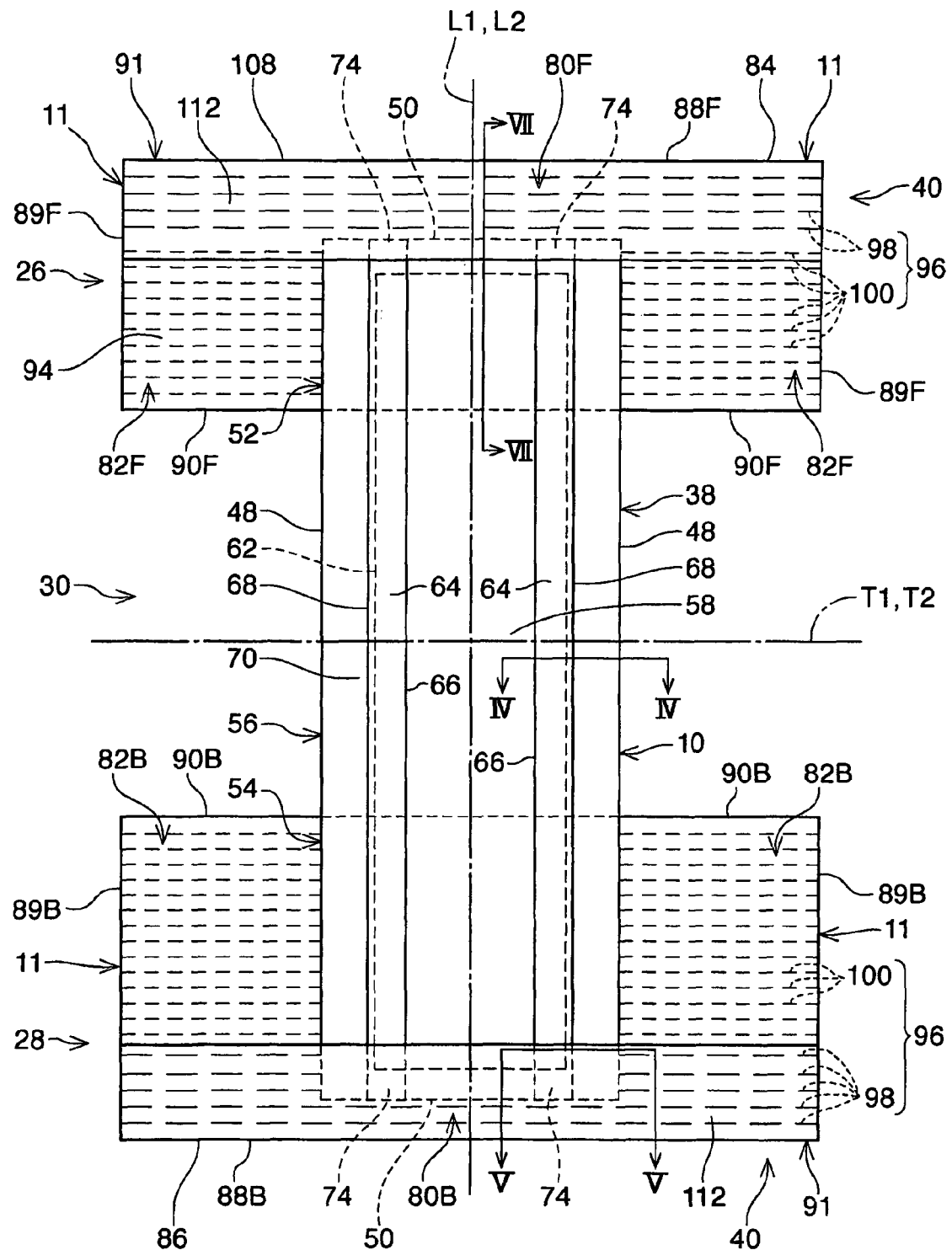
FIG. 2 is a plan view of the pull-on garment in its flat uncontracted condition showing the inner surface.
Figure 3:
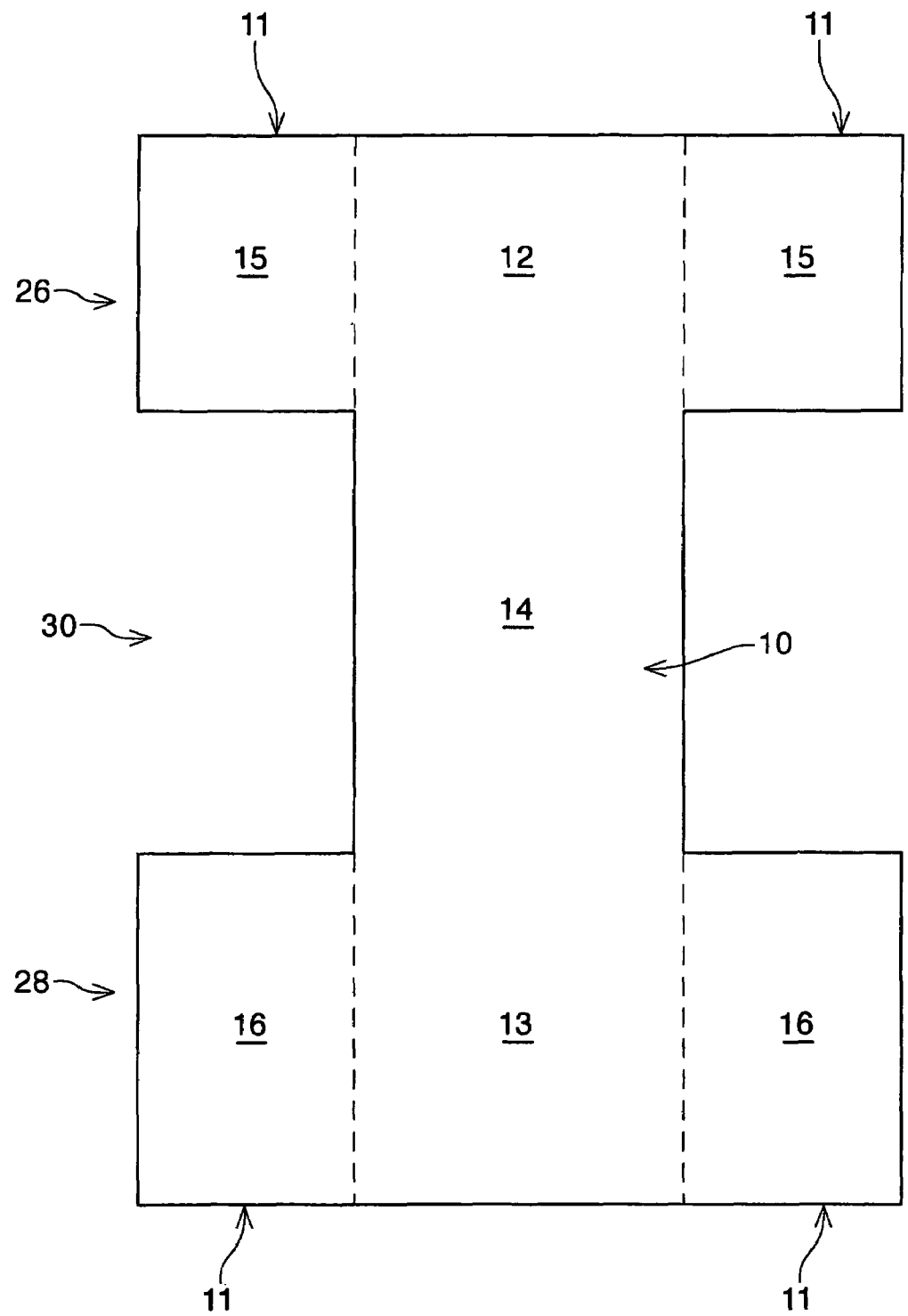
FIG. 3 is a schematic plan view of the pull-on garment in its flat uncontracted condition showing the main portion and the side portion.

In the embodiment shown in FIGS. 1 and 2, the diaper 20 comprises an absorbent main body 38 (hereinafter may be referred to as "main body") to cover the crotch region of the wearer and a belt 40 extending transversely about the waist opening 36. The diaper 20 may also comprise an outer cover layer 42 to cover the main body 38. The belt 40 defines the waist opening 36. The belt 40 and the main body 38 and/or the outer cover layer 42 jointly define the leg opening 34. Alternatively, the belt 40 and the outer cover layer 42 may jointly define the leg opening 34. The pull-on diaper 20 also has a patch sheet 44 printed with a graphic 46 thereon which may be disposed in the front region 26 and/or the back region 28.

The absorbent main body 38 absorbs and contains body exudates disposed on the main body 38. In the embodiment shown in FIG. 2, the main body 38 has a generally rectangular shape having a longitudinal centerline L2, a transverse centerline T2, left and right longitudinally extending side edges 48 (hereinafter may be referred to as "longitudinal side edge") and front and back transversely extending end edges 50 (hereinafter may be referred to as "transverse end edge"). The main body 38 also has waist panels (i.e., a front waist panel 52 positioned in the front waist region 26 of the diaper 20 and a back waist panel 54 positioned in the back waist region 28) and a crotch panel 56 in the crotch region 30 between the front and back waist panels 52, 54.

The belt 40 comprises a front belt 84 and a back belt 86 (hereinafter may be referred to as "front and back belt 84, 86) and has a ring-like configuration by connecting the front belt 84 and the back belt 86. Each of the front belt 84 and the back belt 86 has a central panel 80F, 80B and side panels 82F, 82B contiguous with the central panel 80F, 80B and extending transversely outwardly from the central panel 80F, 80B. Thus, the belt 40 comprises a central panel 80F, 80B and the side panels 82F, 82B. Herein, a portion of a front member and a portion of a back member may be indicated by a reference number with "F" suffix and "B" suffix, respectively, as necessary. Therefore, the "central panel 80F, 80B" for example indicates the "front central panel 80F" and the "back central panel 80B". The "central panel 80" also may mean the "front central panel 80F" and the "back central panel 80B".

Each of the front belt 84 and the back belt 86 has a transversely extending distal edge 88F, 88B, a transversely extending proximal edge 90F, 90B, and longitudinally extending left and right side edges 89F, 89B. Herein, the term "proximal" is used to indicate the position of a "proximal" portion being closer relative to the crotch panel of the main body than the position of a "distal" portion. Therefore, the proximal edge 90F, 90B is located closer than the distal edge 88F, 88B relative to the crotch panel 56 of the main body 38. The front and back belts 84, 86 are joined at or adjacent to the side edges 89F, 89B at the seams 32 to form a pull-on diaper having a waist opening 36 and two leg openings 34. The front central panel 80F may partly or entirely overlap with the front waist panel 52 of the main body 38. The back central panel 80B may partly or entirely overlap with the back waist panel 54 of the main body 38. However, the central panel 80F, 80B does not extend into the crotch panel 56 of the main body 38 and is not disposed in the crotch panel 56. In the embodiment shown in FIG. 2, the central panel 80F, 80B partly overlaps with and is joined to the front waist panel 52 and the back waist panel 54, respectively.

The main portion 10 and the side portion 11 may be formed with separate elements. For example, the side portion 11 may be joined by any known means to the main portion 10, e.g., along the dotted line shown in FIG. 3. Alternatively, the main portion 10 and the side portion 11 may be formed with a single piece of material. For example, the diaper 20 may comprise a piece of chassis layer such as a nonwoven backsheet layer extending into the main portion 10 and the side portion 11 to provide a uni-body of the diaper 20. In the embodiment shown in FIGS. 1, 2 and 3, the main portion 10 comprises the waist panels 52, 54 of the main body 38, the crotch panel 56 of the main body 38, and the central panel 80F, 80B of the belt 40. The side portion 11 comprises the side panels 82F, 82B of the belt 40. The main portion 10 may further comprise a portion of the outer cover layer 42.

Figure 4:
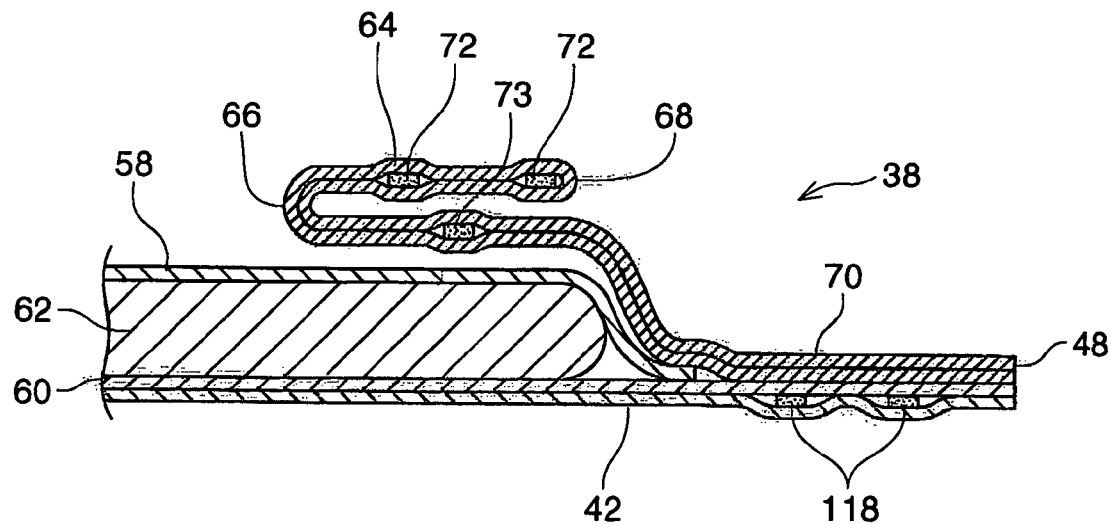
FIG. 4 is a cross-sectional view of FIG. 2 taken along the line IV-IV.
Figure 5:
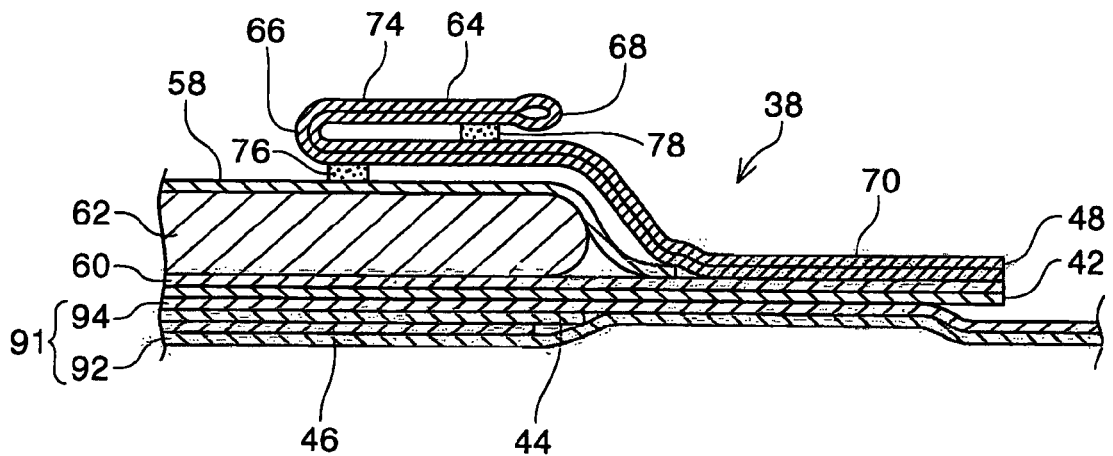
FIG. 5 is a cross-sectional view of FIG. 2 taken along the line V-V.
Figure 6:
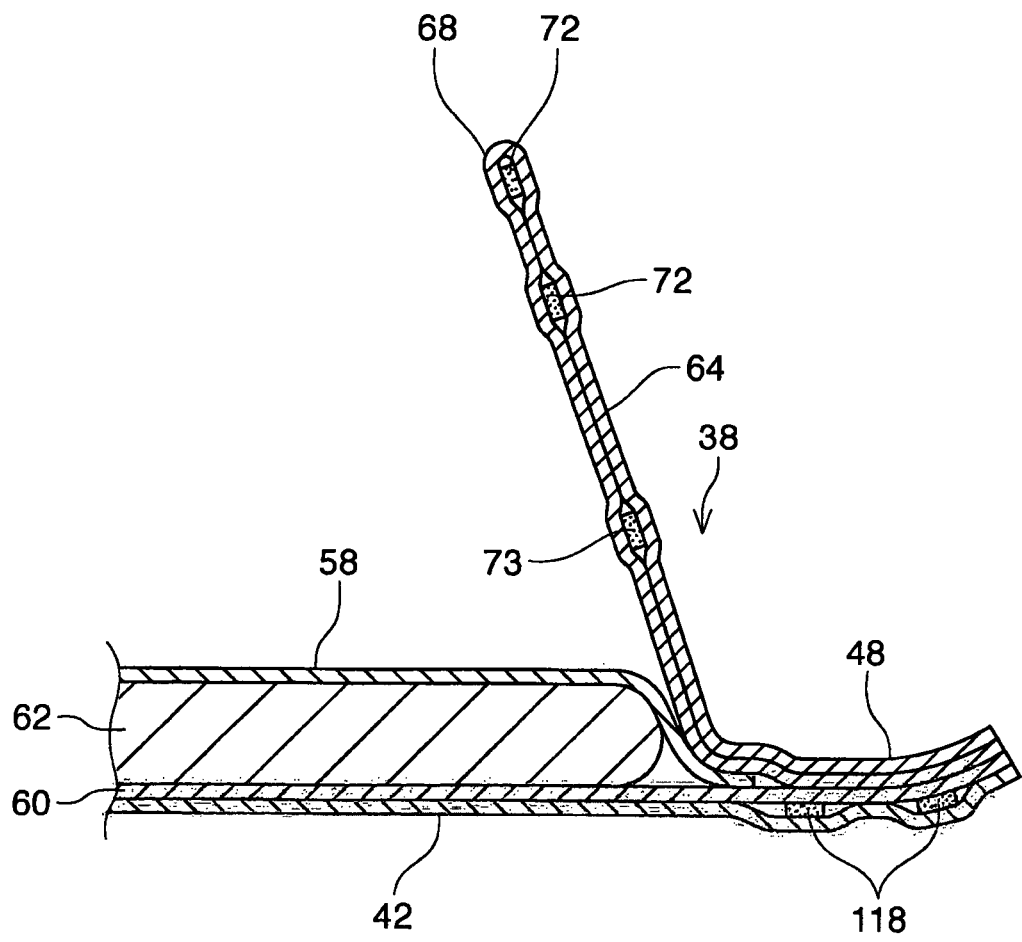
FIG. 6 is a cross-sectional view showing a typical in-use configuration of the portion shown in FIG. 4.

The main body 38 comprises a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 4 comprises a single layer of material which is folded into two layers. The barrier leg cuff 64 extends from the longitudinal side edge 48 toward the longitudinal centerline L2 and then is folded along the folding line 66 back toward the longitudinal side edge 48. The barrier leg cuff 64 has two barrier cuff elastic materials 72 adjacent to the distal portion 68 and one barrier cuff elastic material 73 adjacent to the proximal portion 70 of the barrier leg cuff 64. The proximal portion 70 of the barrier leg cuff 64 is joined to the backsheet 60 adjacent to the longitudinal side edge 48. The portion of the barrier leg cuff 64 along the folding line 66 and the distal portion 68 are free from attachment to any portion of the main body 38 in the crotch panel 56 such that the barrier leg cuff 64 stands up toward the wearer's body as shown in FIG. 6 when the diaper 20 is used. The transverse end 74 of the barrier leg cuff 64 is joined to the topsheet 58 adjacent to the folding line 66 by an attachment means 76 which may be any known means such as an adhesive and is joined onto the barrier leg cuff 64 itself along the distal portion 68 by an attachment means 78 which may be any known means such as an adhesive as shown in FIG. 5.

The liquid pervious topsheet 58 is preferably positioned adjacently the body-facing surface of the absorbent core 62 and may be joined thereto and/or to the backsheet 60 by any attachment means known in the art. The liquid impervious backsheet 60 is generally that portion of the diaper 20 positioned adjacently the garment-facing surface of the absorbent core 62 and prevents the exudates absorbed and contained therein from soiling articles that may contact the diaper 20. The absorbent core is positioned between the topsheet 58 and the backsheet 60 and absorbs and retains liquids such as urine and other certain body exudates. The topsheet 58, the backsheet 60 and the absorbent core may be manufactured any known materials. Suitable topsheet materials may include porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Suitable backsheet materials may include breathable materials that permit vapors to escape from the diaper while still preventing exudates from passing through the backsheet. Suitable absorbent core materials may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The outer cover layer 42 is disposed on the outer surface 22 of the diaper 20 and covers the crotch panel 56 of the absorbent main body 38. The outer cover layer 42 may extend into and cover the front waist panel 52 and the back waist panel 54 of the main body 38. The outer cover layer 42 is directly joined to and covers the liquid impervious backsheet 60 of the main body 38. The central panel 80 of the front and back belt 84, 86 portion is joined to the front waist panel 52 and the back waist panel 54 of the main body 38 through the outer cover layer 42. Thus, the outer cover layer 42 is sandwiched between the front and back belt 84, 86 and the liquid impervious backsheet 60 of the main body 38. In the embodiment shown in FIGS. 2 and 4, the outer cover layer 42 is coextensive with the liquid impervious backsheet 60. The leg elastic material 118 is disposed so as to extend generally longitudinally along the longitudinal side edge 48 of the main body 38. The leg elastic material 118 may be disposed at least in the crotch region 30 of the diaper 20 or may be disposed along the entirety of the longitudinal side edge 48.

The outer cover layer 42 comprises a material separate from the material of the inner layer 94 and the outer layer 92 constituting the belt 40. The outer cover layer 42 may comprise two of more layer of materials. The outer cover layer 42 may comprise any known materials and may comprise materials as used for the front and back belt 84, 86 as explained above. Preferably the outer cover layer 42 comprises a single layer of nonwoven web of synthetic fibers. More preferably, the outer cover layer 42 comprises a single layer of hydrophobic, non-stretchable nonwoven material.

Figure 7:
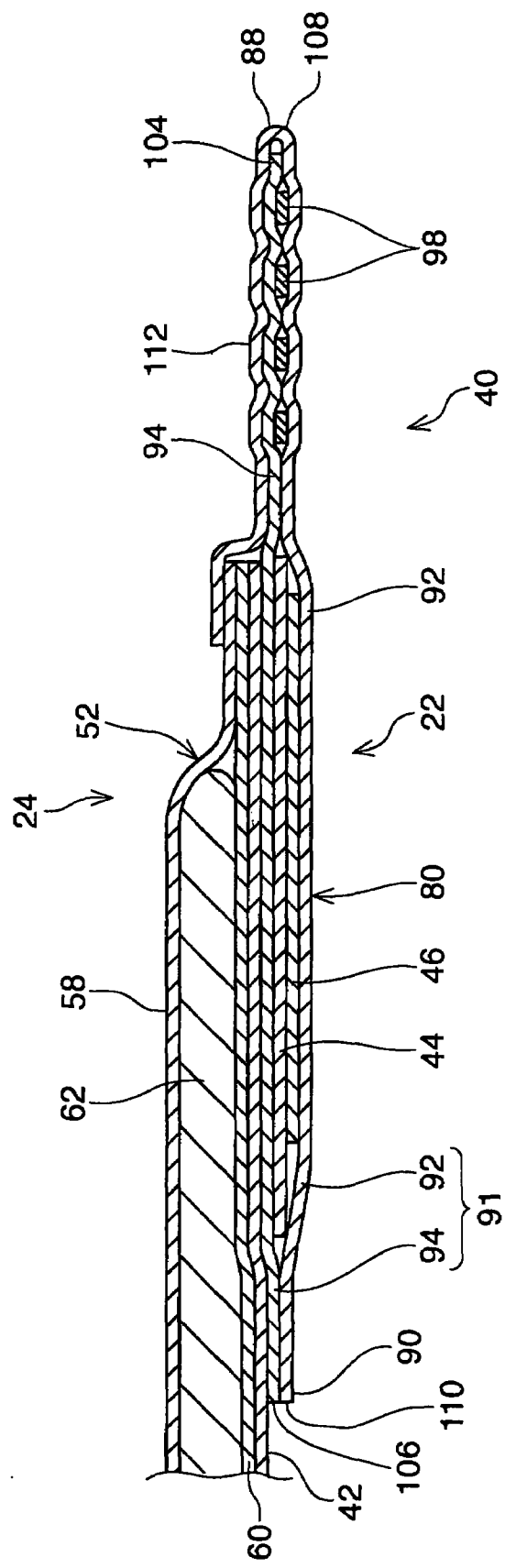
FIG. 7 is a cross-sectional view of FIG. 2 taken along the line VII-VII.

The belt 40 may be ring-like and elastic. The ring-like elastic belt 40 extends transversely about the waist opening 36 of the diaper 20 and acts to dynamically create fitment forces and to distribute the forces dynamically generated during wear. The ring-like elastic belt 40 comprises a belt layer 91 including an outer layer 92. The belt layer 91 may further comprise an inner layer 94. A belt elastic material 96 is interposed between the outer layer 92 and the inner layer 94. The front belt 84 and the back belt 86 may comprise the same materials and/or may have the same structure. Alternatively, the front belt 84 and the back belt 86 may comprise different materials and/or may have different structures. In the embodiment of FIG. 2, the front belt 84 and the back belt 86 generally have the same layer structure. Referring to FIG. 7, the inner layer 94 has a transversely extending distal end 104 and a transversely extending proximal end 106. The outer layer 92 has a transversely extending distal end edge 108 and a transversely extending proximal end edge 110. The inner layer 94 is almost coextensive with the contour of the front and back belt 84, 86. Alternatively, the inner layer 94 may be smaller than the size of the front and back belt 84, 86. The outer layer 92 of the belt layer 91 is longer than the size of the inner layer 94 in the longitudinal direction and an end flap 112 of the outer layer 92 is folded to cover the distal end 104 of the inner layer 94 at the waist opening 36 and to form a distal end edge 108 of the outer layer 92. The inner layer 94 of the belt layer 91 may also have an end flap which may be folded together with the end flap 112 of the outer layer 92. The end flap of the inner layer 94 may be longer or shorter than or equal to the end flap of the outer layer 92. Alternatively, the end flap 112 may be eliminated such that the outer layer 92 terminates at the waist opening 36 to form the distal end edge 108. In the embodiment shown in FIGS. 2 and 7, the distal end edge 108 and the proximal end edge 110 of the outer layer 92 correspond to the distal edge 88 and the proximal edge 90 of the front and back belt 84, 86, respectively. The outer layer 92 surrounded by the distal end edge 108 and the proximal end edge 110 defines the shape of the front and back belt 84, 86 in the embodiment shown in FIGS. 2 and 7.

The front and back belt 84, 86 may comprise any known materials. Suitable material for the front and back belt 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. Preferably the belt comprises a nonwoven web of synthetic fibers. The belt may comprise a stretchable nonwoven. More preferably, the belt comprises an inner hydrophobic, non-stretchable nonwoven material and an outer hydrophobic, non-stretchable nonwoven material.

The belt elastic material 96 comprises a waist elastic material 98 and a side elastic material 100. The waist elastic material 98 may comprise one or more of elastic elements such as strands or panels extending in the transverse direction. The side elastic material 100 also may comprise one or more of elastic elements such as strands or panels extending in the transverse direction. The waist elastic material 98 is continuously disposed along the distal edge 88 of the front and back belt 84, 86. The side elastic material 100 is preferably disposed in the side panel 82 of the front and back belt 84, 86. In the embodiment shown in FIG. 2, the waist elastic material 98 and the side elastic material 100 comprise a plurality of elastic strands which are disposed at a constant interval in the longitudinal direction. Alternatively, the waist elastic material 98 and the side elastic material 100 may be disposed at a different interval in the longitudinal direction. No elastic material may be provided in a portion of the central panel 80 of the front and back belt 84, 86 which overlaps with the absorbent core 62, preferably with the front and back waist panel 52, 54 of the main body 38. Alternatively, no elastic material may be provided in the entirety of the central panel 80. The non-elastic region on the central panel 80 may be formed by cutting the continuously disposed waist elastic material 98 and/or side elastic material 100 in the region of the central panel 80. However, an elastic material may be provided in the central panel 80 if it is necessary.

The belt elastic material 96 in a stretched condition is interposed and joined between the uncontracted outer layer 92 and the uncontracted inner layer 94. When the belt elastic material 96 is relaxed, the belt elastic material 96 returns to the unstretched condition and contracts the outer layer 92 and the inner layer 94. The belt elastic material 96 may provide a desired variation of contraction force in the area of the ring-like elastic belt 40. For example, the contraction force of the front belt 84 may be greater or lower than that of the back belt 86. The contraction force of the waist elastic material 98 may be greater than that of the side elastic material 100, which is typically preferable to provide the diaper 20 with an anchoring force against the wearer at the waist opening 36.

Figure 8:
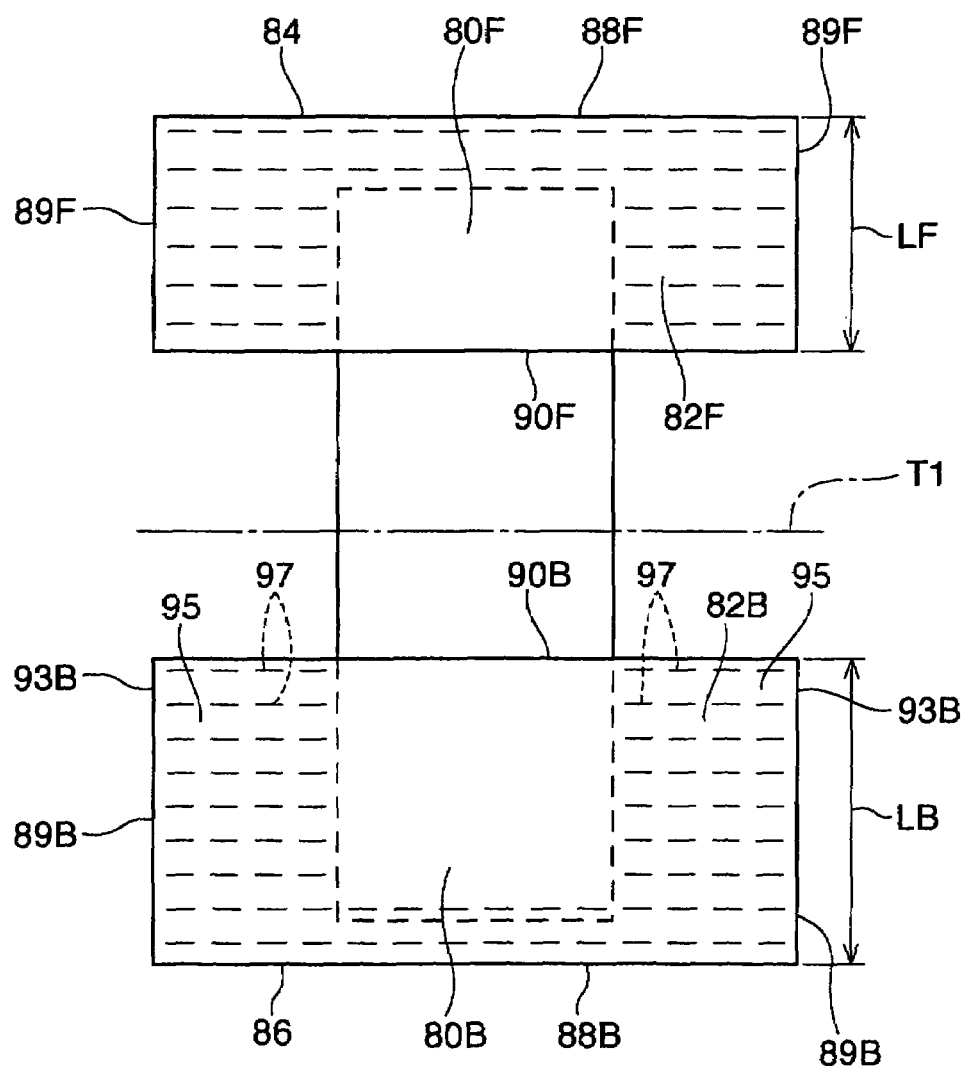
FIG. 8 is a schematic plan view of the garment of the present invention in its flat uncontracted condition showing the outer surface.
Figure 9:
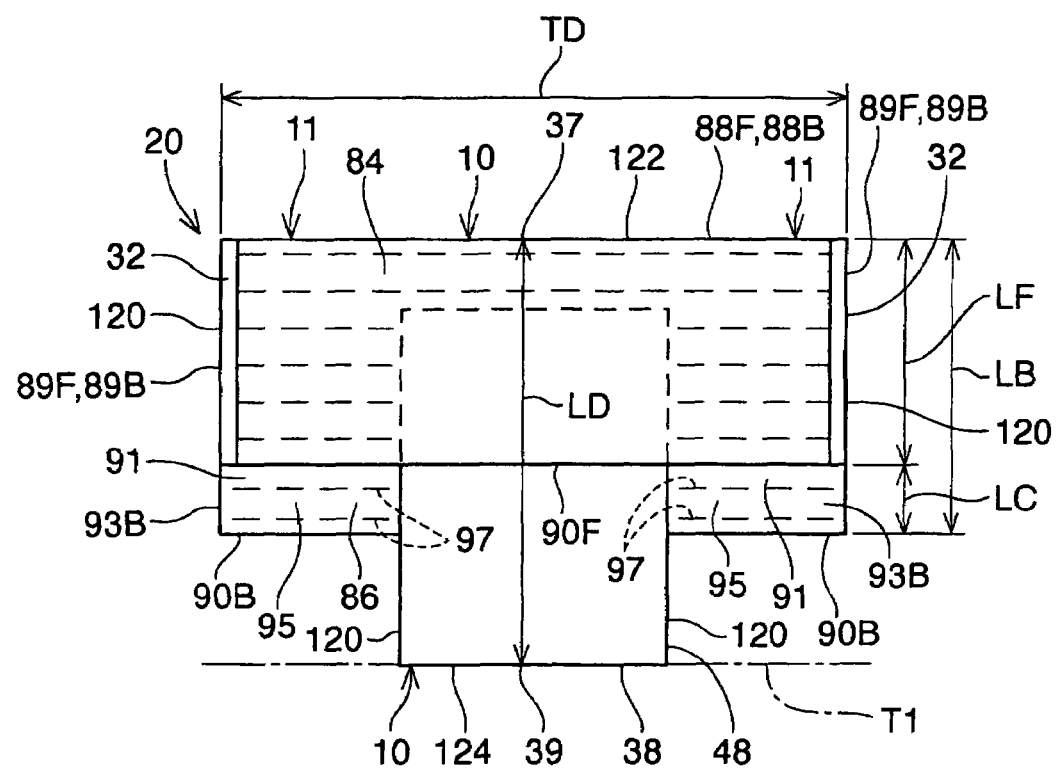
FIG. 9 is a schematic front view of the assembled pull-on garment in its flat uncontracted condition.

The front side panel 82F has a longitudinal length LF defined by the front side edge 89F of the front belt 84 and the back side panel 82B has a longitudinal length LB defined by the back side edge 89B of the back belt 86 (refer to FIGS. 8 and 9). The front belt 84 and the back belt 86 are formed such that the longitudinal lengths LB of the back side panels 82B of the back belt 86 are greater than the longitudinal lengths LF of the front side panels 82F of the front belt 84. The front belt 84 and the back belt 86 are formed by cutting a belt layer web along a cut line. The forming process will be described in detail hereinbelow. In the embodiment shown in FIGS. 8 and 9, the back central panel 80B also has a greater longitudinal length LB between the back distal edge 88B and the back proximal edge 90B than the longitudinal length LF of the front central panel 80F between the front distal edge 88F and the front proximal edge 90F. Therefore, the back belt 86 has a greater longitudinal length LB between the back distal edge 88B and the back proximal edge 90B along its entire width of the back belt 86 in the transverse direction than the longitudinal length LF of the front belt 84 between the front distal edge 88F and the front proximal edge 88F. When the diaper 20 is assembled to form the waist opening 36 and the leg openings 34, the diaper 20 is folded along the transverse centerline T1 such that the front distal edge 88F is aligned with the back distal edge 88B. The front side edge 89F is also aligned with a portion of the back side edge 89B. Then the front panel portion 84 and the back panel 86 portion are joined at or adjacent to the front and back side edges 89F, 89B at the seams 32. The front and back proximal edges 90F, 90B, however, are not aligned to one another as shown in FIG. 9. The back proximal edge 90B is disposed longitudinally closer than the front proximal edge 90F relative to a longitudinally most distant point 39 of the crotch panel 56 from the waist opening edge 37 such that the proximal portion 93B of the back side panel 82B extends toward the crotch panel 56 of the main body 38 beyond the front proximal edge 90F. Thus, the proximal portion 93B of the back side panel 82B provides a buttock cover 95. The side edge of the proximal portion 93B is not joined to anywhere and is free from attachment.

The dimension of the buttock cover 95 can be selected to provide an effective function of buttock cover. The ratio of the longitudinal length LB of the back side edge 89B to the longitudinal length LF of the front side edge 89F is preferably between about 1.1 and about 2.0, more preferably between about 1.1 and about 1.5 in a laid out flat configuration of the garment. The longitudinal length LC shown in FIG. 9 is the difference between LB and LF to provide the buttock cover 95. The ratio of the length LC to the length LF is preferably between about 0.1 and about 1.0, more preferably about 0.1 and about 0.5 in a laid out flat configuration of the garment. The longitudinal garment length LD is the distance from the waist opening edge 37 to a longitudinally most distant point 39 of the crotch panel 56 from the waist opening edge 37 when the garment is laid out flat. The longitudinal length LB of the back side edge 89B is preferably between about 50% and 100%, more preferably about 60% and about 80% of the longitudinal garment length LD when the garment is laid out flat. The garment having these dimension characteristics provides an effective buttock cover without hindering the wearer from inserting legs into the leg opening.

Figure 10:
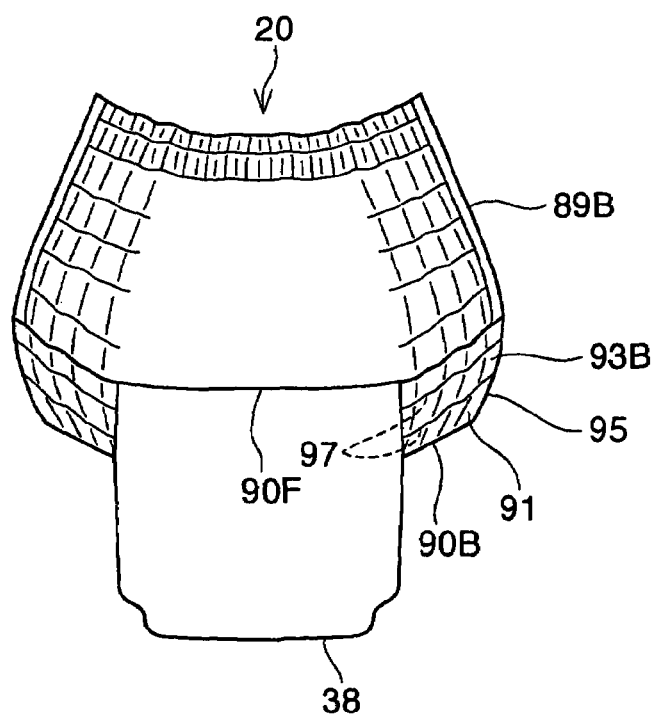
FIG. 10 is a schematic front view of the assembled pull-on garment in its contracted condition.
Figure 11:
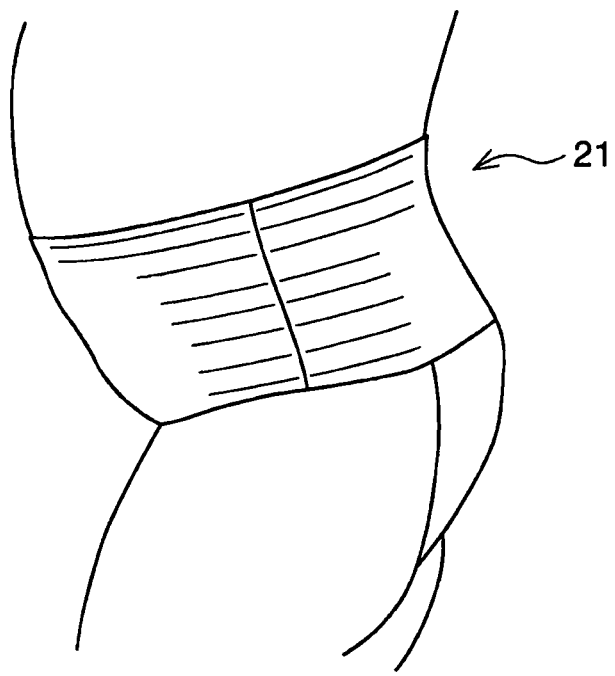
FIG. 11 is a schematic side view of the garment in its use condition for comparison.
Figure 12:
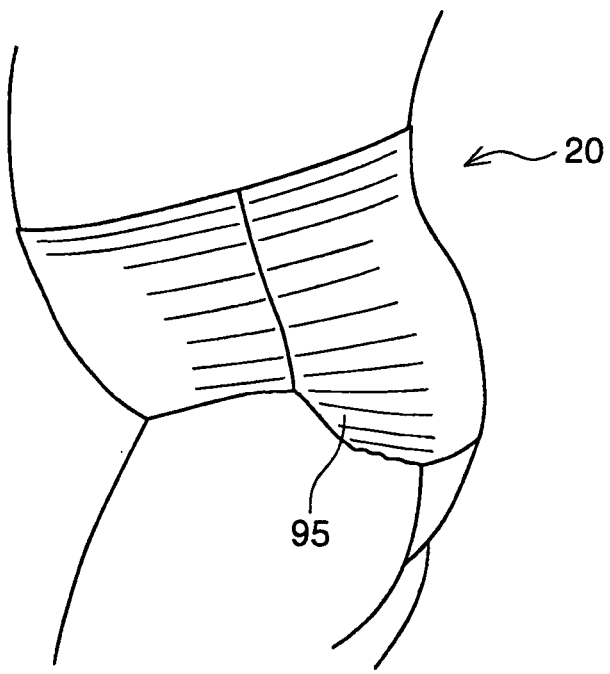
FIG. 12 is a schematic side view of the garment of the present invention in its use condition.

The buttock cover 95 has a buttock cover elastic material 97. The buttock cover elastic material 97 may be a portion of the belt elastic material 98 and be formed with the same material as the belt elastic material 96. The buttock cover elastic material 97 preferably has greater contraction force than the side elastic material 100 on the back side panel 82B. The greater contraction force of the buttock cover elastic material 97 helps gathering the belt layer 91 to provide an aesthetic appearance with the buttock cover 95. FIG. 10 shows the diaper 20 in a contracted condition. As shown, since the buttock cover elastic material 97 gathers the belt layer 91 generally transversely, the proximal portion 93B of the back side panel 82B is pulled to reduce angular appearance of the buttock cover 95. FIGS. 11 and 12 show a diaper worn by a wearer. The diaper 21 shown in FIG. 11 does not have a buttock cover and can not sufficiently cover the buttock of the wearer. However, the diaper 20 of the present invention shown in FIG. 12 has a buttock cover 95 and sufficiently covers the buttock of the wearer.

Shown in FIG. 13 is a diaper 20 in a flat contracted and unfolded condition. The diaper 20 comprises the waist elastic material 98 which extends along the waist opening 36 from one side (e.g., left side) of the side portion 11 through the main portion 10 to the other side (e.g., right side) of side portion 11, to provide sufficient stretchability around the wearer's waist. The diaper 20 also comprises the side elastic material 100 extending only on the side portion 11 so that the elastic material does not contract the main body 38 or the absorbent core 62 so much. In addition, the contraction force of the waist elastic material 98 may be greater than that of the side elastic material 100 to provide the diaper 20 with an anchoring force against the wearer at the waist opening 36. The diaper 20 somewhat deforms due to such an arrangement of the waist elastic material 98 and the side elastic material 100 as shown in FIG. 13 when the diaper 20 is in a flat contracted and unfolded condition, while the transverse width TD (refer to FIG. 9) at the side portions 11 is constant along the longitudinal centerline L1 when the diaper 20 is in a flat uncontracted and unfolded condition. The deformation of the diaper 20 is such that contracted width (i.e., TD-TF) between the longitudinal side contour lines 120 at the waist opening 36 is greater than contracted width (i.e., TD-TS) between the longitudinal side contour lines 120 at the side portions 11. As the result, the transverse width at the waist opening 36 becomes shorter than the transverse width at the side portions 11, specifically shorter than the transverse width at the side portion 11 adjacent to the leg openings 34.

In the configuration shown in FIG. 13, the diaper 20 has a first transverse width TF between the longitudinal side contour lines 120 at the waist opening 36 and a second transverse width TS between the longitudinal side contour lines 120 at the side portions 11 adjacent to the leg openings 34. The longitudinal side contour line 120 is formed with the side edge 89F, 89B of the belt 40, the proximal edge 90B of the back belt 86 and the longitudinal side edge 48 of the main body 38 in FIG. 13. The first transverse width TS in FIG. 13 is the straight distance between the left point 130 of intersection of the distal edge 88F, 88B of the belt 40 with the left side edge 89F, 89B and the right point 132 of intersection of the distal edge 88F, 88B with the right side edge 89F, 89B. The second transverse width TS is greater than the first transverse width TF and is the greatest transverse width at the side portions 11. The second transverse width TS in FIG. 13 is the straight distance between the left point 134 of intersection of the proximal edge 90F of the front belt 84 with the left side edge 89F and the right point 136 of intersection of the proximal edge 90F of the front belt 84 with the right side edge 89F.

Alternatively, the second transverse width TS may be positioned anywhere on the side portions depending on the diaper shape in its contracted condition, other than the portion of the first transverse width TS. The second transverse width TS is typically positioned adjacent to the leg openings 34. Herein the term "adjacent to the leg opening" means that the portion of the side portions 11 having the second transverse width TS is closer to the leg openings 34 than the portion of the waist opening having the first transverse width TF.

The waist elastic material 98 contracts and deforms not only a portion of the diaper 20 along the waist opening 36 but also the transverse end edge 50 of the absorbent main body 38. The longitudinal side edges 48 of the absorbent main body 38 also deform to shorten the transverse width between the longitudinal side edges 48 as it comes closer to the transverse end edge 50. As the absorbent main body 38 deforms, the absorbent core 62 also similarly deforms. The longitudinal side edge 63 of the absorbent core 62 deforms to incline toward the longitudinal centerline L1 (not shown in FIG. 13) as it comes to closer to the transverse end edge 50.

The longitudinal side contour line 120 at the side portion 11 has an inclination with respect to the longitudinal direction of the diaper 20. The longitudinal side contour line 120 becomes more distant from the longitudinal centerline L1 as it gets closer to the leg openings 34 when the side portion 11 is unfolded as shown in FIG. 13. The inclination with respect to the longitudinal direction of the diaper 20 may have an angle A of between 10 degree to 30 degree when the side potion 11 is unfolded. It can be between 10 degree and 45 degree. The angle A is expressed in a positive number when the longitudinal side contour line 120 inclines to become more distant from the longitudinal centerline L1 as it gets closer to the leg openings 34 as shown in FIG. 13. The degree of the angle A is expressed in a negative number when the longitudinal side contour line 120 inclines to become more distant from the longitudinal centerline L1 as it gets closer to the waist opening 36. When the inclination falls within the range of angle A above, the diaper 20 is aesthetically pleasing to consumers as a pant-like undergarment. The longitudinal side contour line 120 at the side portion 11 may extend straightly or curvedly. When the longitudinal side contour line 120 is curved, the inclination may be determined by the straight line connecting the point on the longitudinal side contour line 120 at the first transverse width TF and the point on the longitudinal side contour line 120 at the second transverse width TS. For example, the inclination may be determined by the straight line connecting the point 130 and the point 134 or the straight line connecting the point 132 and the point 136 if the longitudinal side contour line 120 in FIG. 13 is curved.

In contrast to consumer benefits of the pant-like aesthetic appearance, such a configuration of the diaper 20 is less advantageous to package an array of the diapers 20 into a package comprising, e.g., a thin flexible plastic film since such a flexible package does not help to form a well-balanced parallelepiped due to the projecting side portions 11. As the result, stackability of the packages deteriorates. In order to improve stackability of the packages, therefore, the side portions 11 are folded along a folding line 126 toward the longitudinal centerline L1 when the diaper 20 is contained in a package such that the second transverse width TS decreases and the difference between the first transverse width TF and the second transverse width TS decreases when the side portions 11 are folded compared with when the side portions 11 are unfolded. By folding the side potions 11 in such a way, the diaper 20 forms a new longitudinal side contour line 120 comprising the folding line 126. The side portion 11 may be folded generally parallel to the longitudinal centerline L1 or may be folded non-parallel to the longitudinal centerline L1. The side portion 11 may be folded along a straight line or along a curved line.

The side portion 11 is folded along a straight folding line 126 extending generally parallel to the longitudinal centerline L1 in the embodiment shown in FIG. 14. The side portion 11 is folded such that the folded width TB of the side portion 11 adjacent to the leg opening 34 is greater than the folded width TA of the side portion 11 at the waist opening 36. As the result, the angle of the inclination of the longitudinal side contour line 120 decreases with respect to the longitudinal direction of the diaper 20. The inclination with respect to the longitudinal direction of the diaper 20 may have an angle A of between −5 degree to 5 degree when the side potion 11 is folded. It can be between −9 degree and 9 degree. Herein, whether the angle decreases is determined by comparing the absolute number of the angle before and after the side portion 11 is folded. It is apparent that the angle decreases when the angle changes from 15 degree to 3 degree for example before and after the side portion 11 is folded. The angle also decreases when the angle changes from 15 degree to −3 degree for example before and after the side portion 11 is folded. In FIG. 14, the angle of the inclination of the longitudinal side contour line 120 is about 0 degree. In addition, the difference between the first transverse width TF and the second transverse width TS decreases and the first transverse width TF and the second transverse width TS become the almost same. Instead of the straight folding line 126 extending generally parallel to the longitudinal centerline L1, the side portion 11 may be folded along a straight or curved folding line which is inclined with respect to the longitudinal direction of the diaper 20 as far as the difference between the first transverse width TF and the second transverse width TS decreases. The side portion 11 may be folded such that the first transverse width TF is a little narrower than the second transverse width TS or a little wider than the second transverse width TS. When the first transverse width TF is a little wider than the second transverse width TS, the angle of the inclination of the longitudinal side contour line 120 takes a negative number.

Figure 15:
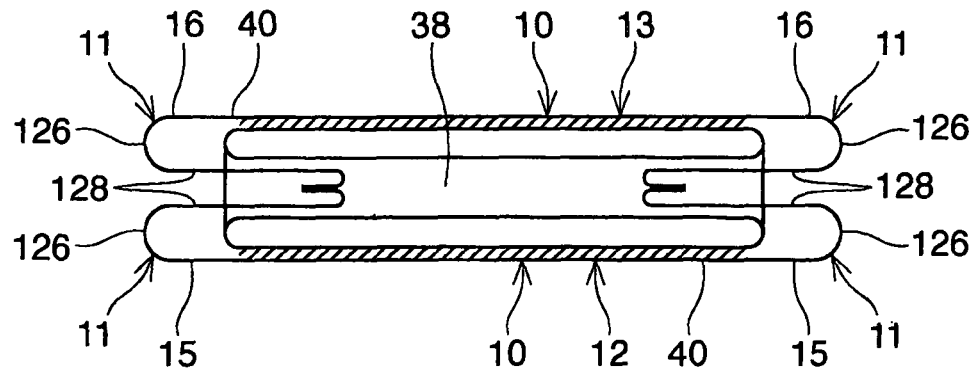
FIG. 15 is a schematic top plan view of the assembled pull-on garment with the side portion folded.
Figure 16:
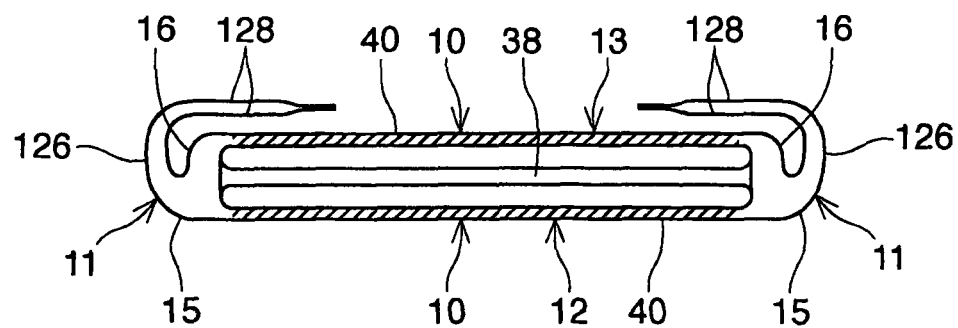
FIG. 16 is a schematic top plan view of an alternative embodiment of the assembled pull-on garment with the side portion folded.

The side portion 11 may be folded along the folding line 126 disposed laterally outside the main portion 10 such that the main portion 10 is not folded. Therefore, the folding line 126 may generally longitudinally extend on the side portion 11 to fold a portion of the side portion or the belt 40 without folding a portion of the main portion 10 or the main body 38. However, a portion of the main portion 10 may be folded along the folding line 126. It is preferable that the folding line 126 extends on the side portion 11 for easiness of folding since the side portion 11 is typically less bulky than the main portion 10. The side portion 11 may be folded such that the folded portion 128 of the side portion 11 is sandwiched directly between the front side portion 15 and the back side portion 16 and directly between the front main portion 12 and the back main portion 13 as shown in FIG. 15. Alternatively, the folded portion 128 may be sandwiched only between the front side portion 15 and the back side portion without the folded portion 128 extending into the main portion 13 or may be sandwiched directly only between the front main portion 12 and the back main portion 13. Such an arrangement is possible by selecting the position of the folding line 126 on the diaper 20. Further alternatively, the folded portion 128 may be folded backward onto the outside of the back main portion 13 as shown in FIG. 16 or may be folded forward onto the front main portion 12.

Figure 17:
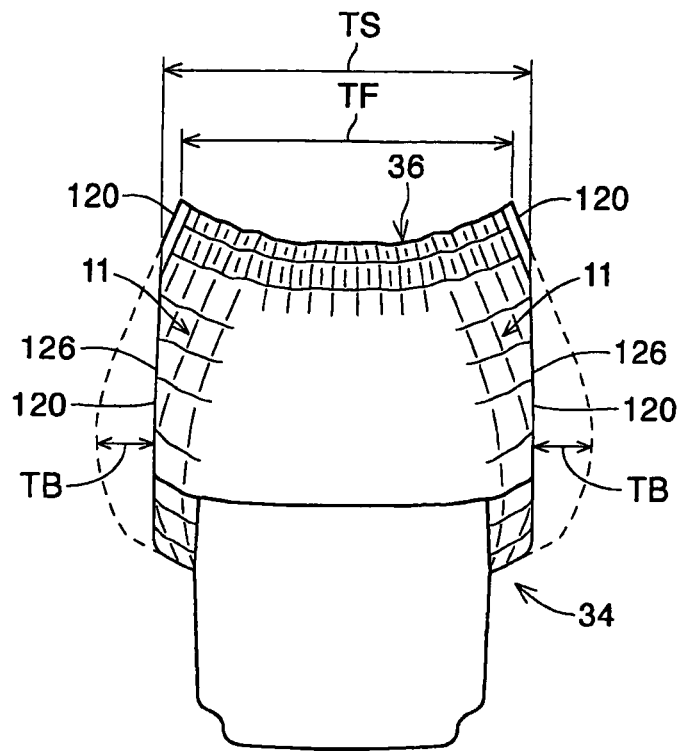
FIG. 17 a schematic front view of an alternative embodiment of the assembled pull-on garment with the side portion folded.

FIG. 17 shows the side portion 11 which is folded along a straight folding line 126 extending generally parallel to the longitudinal centerline L1 (not shown in FIG. 17). The straight folding line 126, however, does not extend between the waist opening 36 and the leg opening 34, but only extends such that the side portion 11 adjacent to the leg opening 34 is folded and the side portion 11 at the waist opening 36 is not folded. Therefore, the second transverse width TS decreases by the folded width TB while the first transverse width TF does not change before and after the side portion is folded. As the result, the difference between the first transverse width TF and the second transverse width TS decreases when the side portions 11 are folded compared with when the side portions 11 are unfolded.

Figure 18:
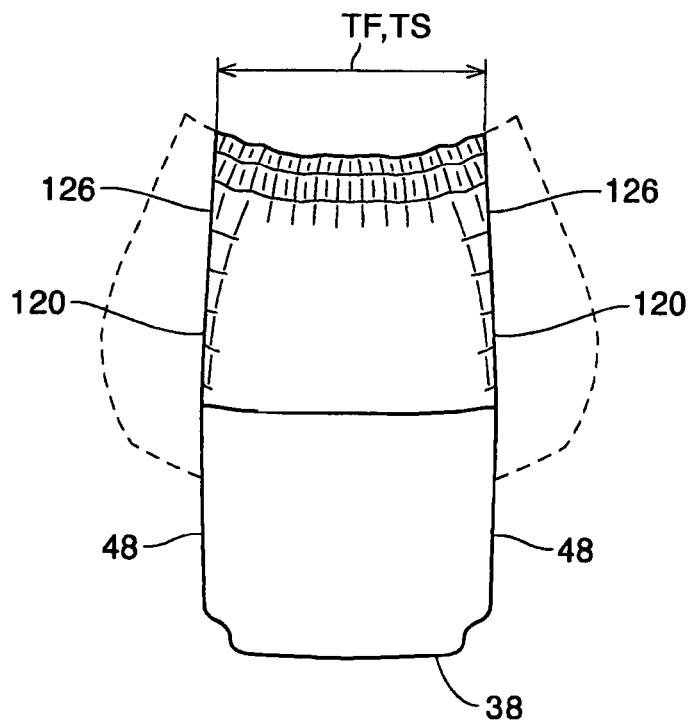
FIG. 18 a schematic front view of an alternative embodiment of the assembled pull-on garment with the side portion folded.

FIG. 18 shows the side portion 11 which is folded along a straight folding line 126 extending generally parallel to the longitudinal centerline L1. The side portion 11 is folded such that the straight folding line 126 aligns with the longitudinal side edge 48 of the main body 38 to form a straight longitudinal side contour line 120. In FIG. 18, the side portion 11 is folded such that the first transverse width TF and the second transverse width TS are the almost same.

The patch sheet 44 printed with a graphic 46 is provided on the diaper 20 to provide an aesthetic appearance. The graphic 46 may be any graphic to enhance aesthetic appearance, such as visual characters, educational signs or marks. The patch sheet 44 may comprise any known material such as a vapor permeable or vapor impermeable plastic film, a woven, a nonwoven, tissues or paper and may have any shape. The patch sheet 44 may also comprise a single sheet or two or more separate sheets. In the embodiment shown in FIG. 1, the patch sheet 44 comprises a single rectangular nonwoven having high breathability. The printing may be made by any known process such as flexographic printing, ink-jet printing, screen printing, or rotogravure printing.

The patch sheet 44 is a material separate from any elements constituting the diaper 20. The patch sheet 44 may be joined anywhere as far as it can be seen by the user of the diaper. The patch sheet 44 is preferably joined somewhere outside the liquid impervious backsheet 60 of the main body 38, preferably outside the outer cover layer 42, more preferably outside the inner layer 94 of the front and back belt 84, 86 to reduce hazy appearance of the graphic 46. The patch sheet 44, however, is joined inside the outer layer 94 of the front and/or back belt 84, 86 to prevent an ink rub-off problem caused by abrasion of the ink layer of the graphic 46 with other substrates such as cloths or floors. Alternatively, the patch sheet 44 may be joined outside the outer layer 94 of the front and/or back belt 84, 86 to further reduce hazy appearance of the graphic 46. In such a case, it is preferable that the printed surface of the patch sheet 44 is disposed to face the outer layer 94 to prevent an ink rub-off problem. If the ink withstands the rub-off, the printed surface of the patch sheet 44 may face the outside of the diaper 20. In the embodiment shown in FIG. 7, the patch sheet 44 with the graphic 46 is disposed and joined between the inner layer 92 and the outer layer 94 of the front and back belt 84, 86. However, if the front and back belt 84, 86 of the diaper 20 is formed with only the belt elastic material 96 and the outer layer 94 and does not have the inner layer 92, the patch sheet 44 may be disposed between the liquid impervious backsheet 60 of the main body 38 and the outer layer 94 of the front and back belt 84, 86. In such a case, the patch sheet 44 may be joined to the liquid impervious backsheet 60, the outer layer 94 or both of them.

The position of the patch sheet 44 is selected such that the patch sheet 44 is disposed between the distal end edge 108 and the proximal end edge 110 of the front and back belt 84, 86. The distal end edge 108 and the proximal end edge 110 do not cross any portion of the graphic 46 (refer to FIG. 1). The entirety of the graphic 46 is covered by only the outer layer 92. Therefore, the graphic appearance is the substantially same anywhere in the patch sheet 44 not to make a part of the graphic 46 to have hazier appearance than other parts of the graphic 46.

The patch sheet 44 is preferably disposed in the central panel 80 of the front and back panel portion 84, 86 in which the belt elastic material 96 is not present as shown in FIG. 1. However, the patch sheet 44 may be disposed in the area such as in the side panel 82 in which the belt elastic material 96 is present. The patch sheet 44 may be coextensive with the outer layer 92 of the front and back belt 84, 86 such that the patch sheet 44 has the same shape as the outer layer 92. However, it is preferable that the patch sheet 44 is smaller than the outer layer 92 to reduce bulkiness of the front and back belt 84, 86. The front and back belt 84, 86 may have two or more patch sheets with a graphic which are disposed between the distal end edge 108 and the proximal end edge 110 of the front and back belt 84, 86.

Figure 19:
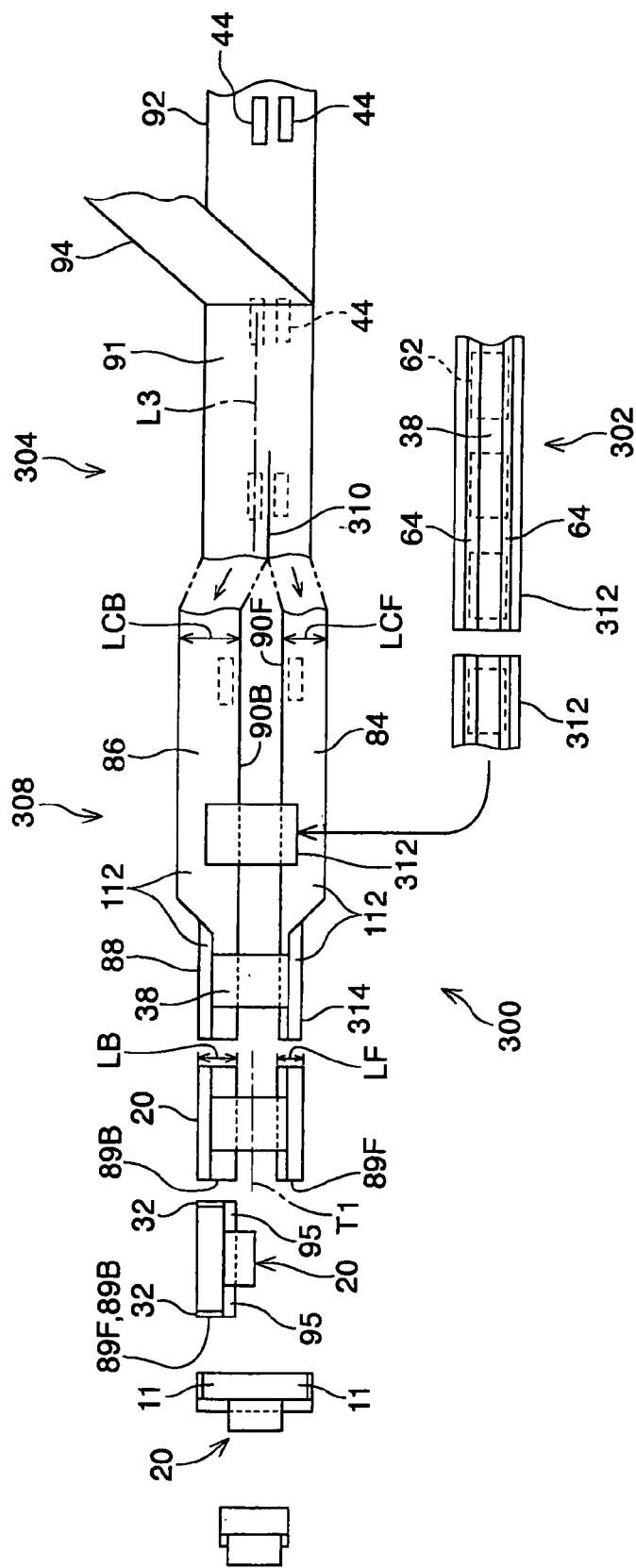
FIG. 19 is a schematic view showing the process for forming the pull-on garment shown in FIG. 1.

FIG. 19 shows a schematic view to explain the process for forming the diaper 20. The process 300 shown in FIG. 19 primarily comprises three sections; a main body forming section 302, a belt forming section 304 and an assembly section 308. Since FIG. 19 is a schematic view, it should be noted that various parts of the diaper have been omitted, such as the belt elastic material and the leg elastic material.

The main body forming process 302 combines elements forming the main body 38 such as the topsheet 58, the backsheet 60, the absorbent core 62 and the barrier leg cuff 64 such that the absorbent core 62 is sandwiched between the topsheet 58 and the absorbent core 62. The outer cover layer 42 (not shown in FIG. 19) is joined to the backsheet 60 (not shown in FIG. 19) and the leg elastic material 118 (not shown in FIG. 19) is sandwiched between the backsheet 60 and the outer cover layer 42. These elements are joined to each other by any known means such as adhesives or heat bonding to form an intermediate assembly 312. The intermediate assembly 312 then cut into the individual intermediate assembly 312. The individual intermediate assembly 312 is turned by 90 degree and fed into the assembly section 308.

Figure 20:
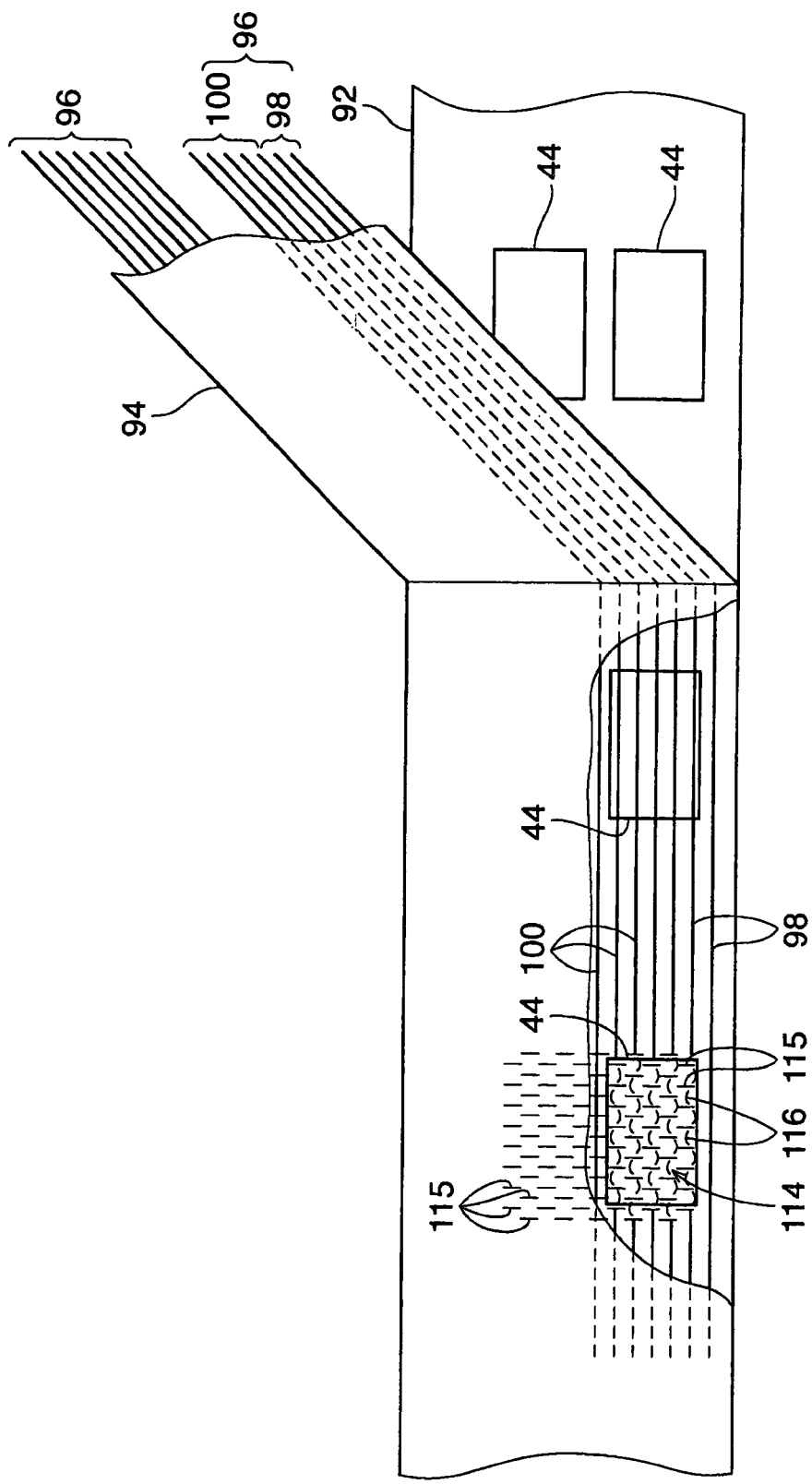
FIG. 20 is a schematic view showing the process for sandwiching the belt elastic material and the patch sheet between the outer layer web and the inner layer web and subsequently cutting the belt elastic material.

The belt forming section 304 combines the outer layer web 92 and the inner layer web 94 to form a continuous belt layer web 91. When joining the outer layer web 92 and the inner layer web 94, the patch sheet 44 is sandwiched therebetween. In the embodiment shown in FIG. 19, two patch sheets 44 (one comes to the front of the diaper 20 and the other comes to the back of the diaper 20) are placed on the outer layer web 92. The two of patch sheet may be placed on the outer layer web 92 by two separate apparatuses, each of which handles and places one patch sheet, or by a single apparatus which handles and places two patch sheets. In addition, the belt elastic material 96 (shown in FIG. 20) is sandwiched between the outer layer web 92 and the inner layer web 94. After that, the belt elastic material 96 is cut to form a non-elastic or weakened elastic region 114 in a portion of the central panel 80 of the front and back belt 84, 86. The belt elastic material 96 is cut through the outer layer web 92, the patch sheet 44 and the inner layer web 94 by, e.g., a die cutter or an apparatus applying heat and/or pressure at a plurality of cut portions 115. The belt elastic material 96 is cut into a plurality of elastic material pieces 116 between the cut portions 115 and the elasticity thereof is eliminated or weakened.

Figure 21:
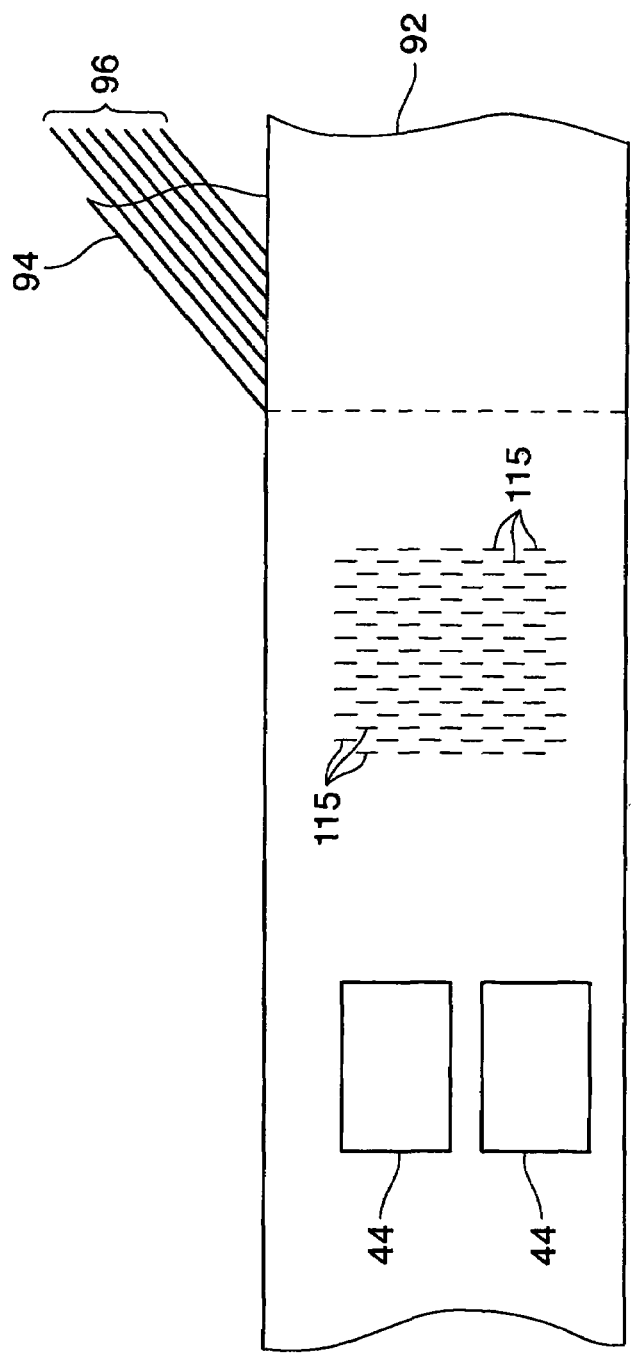
FIG. 21 is a schematic view showing the process for sandwiching the belt elastic material between the outer layer web and the inner layer web, cutting the belt elastic material and subsequently placing the patch sheet outside the outer layer web.

Instead of sandwiching the patch sheet 44 and the belt elastic material 96 between the outer layer web 92 and the inner layer web 94 and subsequently cutting the belt elastic material 96 through the outer layer web 92, the patch sheet 44 and the inner layer web 94, the only belt elastic material 96 may be first sandwiched between the outer layer web 92 and the inner layer web 94 and subsequently cut through the outer layer web 92 and the inner layer web 94 at a plurality of cut portions 115 as shown in FIG. 21. After that, the patch sheet 44 is placed and joined outside the outer layer web 92. The patch sheet 44 being positioned outside not only improves visibility of the graphic 46 but is able to hide the cut portions 115 formed onto the outer layer web 94 to further enhance the aesthetic appearance of the diaper 20. The patch sheet 44 may be placed so that the graphics faces the outside of the diaper 20 or the outer surface of the outer layer web 94. The patch sheet 44 may be placed and joined inside the inner layer web 94.

The continuous belt layer web 91 is cut along a straight cut line 310 which corresponds to the proximal edge 90F, 90B to form a continuous front belt web 84 and a continuous back belt web 86. The cut line 310 is biased from the longitudinal centerline L3 of the continuous belt layer web 91 to differentiate the length LCF of the continuous front belt web 84 and the length LCB of the continuous back belt web 86 in the cross machine direction. The cross machine direction means the direction crossing the machine direction at a right angle. The machine direction means the direction where the component material is conveyed in the manufacturing process, which is in parallel to the longitudinal centerline L3. The continuous front belt web 84 and the continuous back belt web 86 are separated from one another.

The assembly section 308 combines the individual intermediate assembly 312 with the continuous front belt web 84 and the continuous back belt web 86. The individual intermediate assembly 312 is placed on the continuous front and back belt webs 84, 86 at a predetermined interval to provide the side panel between each of the individual intermediate assemblies 312. The end flap 112 of the front and back belt webs 84, 86 is folded inwardly along the distal edge 88 to form a continuous diaper assembly 314 comprising the main body 38, the outer cover layer 42 (not shown in FIG. 19) and the front and back belt webs 84, 86. The continuous diaper assembly 314 thus formed is cut into each individual diaper 20. The individual diaper 20 has the longitudinal length LB of the back side edge 89B being greater than the longitudinal length LF of the front side edge 89F. The individual diaper 20 is then folded along the transverse centerline T1 in the crotch region and the front and back belt 84, 86 is joined at the seam 32 adjacent to the side edges 89F, 89B to form the waist opening and the leg openings. The buttock cover 95 is also formed as shown in FIG. 19 without requiring trimming any portion of the belt layer web. The individual diaper 20 is then turned by 90 degree so that the longitudinal centerline L1 of the diaper 20 orients the machine direction. The side portion 11 are finally folded such that the second transverse width TS decreases and the difference between the first transverse width TF and the second transverse width TS decreases when the side portions 11 are folded compared with when the side portions 11 are unfolded as explained above.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A disposable pull-on garment contained in a package, the pull-on garment having a waist opening and leg openings, and having a longitudinal centerline and a transverse centerline, the pull-on garment comprising a main portion and side portions extending transversely outwardly from the main portion wherein said main portion and said side portions are formed with separate elements and said side portions are joined to said main portion, said main portion comprising a liquid pervious topsheet, a liquid impervious backsheet, an absorbent core disposed between the topsheet and the backsheet, a leg elastic material and a barrier leg cuff, said side portions comprising an elasticized front side panel comprising a side elastic material extending in a transverse direction of said main portion, a longitudinally extending distal side edge having a longitudinal length and a back side panel comprising a longitudinally extending distal side edge having a longitudinal length that is greater than the longitudinal length of said longitudinally extending distal side edge of said front side panel, wherein the front side panel and the back side panel are joined at a seam to form said waist and leg openings, the pull-on garment having longitudinal side contour lines to define a transverse width of the pull-on garment, the pull-on garment having a first transverse width between the longitudinal side contour lines at the waist opening and a second transverse width between the longitudinal side contour lines at the seam of the front and back side panels, the second transverse width being greater than the first transverse width and being the greatest transverse width at the side portions in a flat contracted and unfolded condition of the pull-on garment, wherein
the side portions are folded along a folding line toward the longitudinal centerline when the pull-on garment is contained in a package such that the second transverse width decreases and the difference between the first transverse width and the second transverse width decreases when the side portions are folded compared with when the side portions are unfolded.

2. The disposable pull-on garment of claim 1 wherein the longitudinal side contour line at the side portion has an inclination with respect to the longitudinal direction of the pull-on garment to become more distant from the longitudinal centerline as it gets closer to the leg openings when the side portion is unfolded, and the angle of the inclination of the longitudinal side contour line decreases with respect to the longitudinal direction of the pull-on garment when the side portion is folded.

3. The disposable pull-on garment of claim 1 or 2 wherein the transverse width at the side portions is constant along the longitudinal centerline when the pull-on garment is in a flat uncontracted and unfolded condition.

4. The disposable pull-on garment of claim 1 wherein the folded width of the side portion adjacent to the leg opening is greater than the folded width of the side portion adjacent to the waist opening.

5. The disposable pull-on garment of claim 1 wherein the side portion adjacent to the leg opening is folded and the side portion at the waist opening is not folded.

6. The disposable pull-on garment of claim 1 wherein the side portion is folded along the folding line disposed laterally outside the main portion such that the main portion is not folded.

7. The disposable pull-on garment of claim 1 wherein the pull-on garment comprises an absorbent main body and a belt, the absorbent main body comprises waist panels and a crotch panel between the waist panels, the belt comprises a central panel and side panels transversely outwardly extending from the central panel, wherein the main portion comprises the waist panels, the crotch panel and the central panel, and the side portion comprises the side panels.

8. The disposable pull-on garment of claim 1 wherein the side portion comprises a front side portion and a back side portion, and the side portion is folded such that the folded portion of the side portion is sandwiched between the front side portion and the back side portion.

9. The disposable pull-on garment of claim 1 or 8 wherein the main portion comprises a front main portion and a back main portion, and the side portion is folded such that the folded portion of the side portion is sandwiched between the front main portion and the back main portion.

* * * * *